United States Patent
Autelitano et al.

(10) Patent No.: US 7,456,148 B2
(45) Date of Patent: Nov. 25, 2008

(54) METHOD OF PRODUCING AN ANTICOAGULATION EFFECT

(75) Inventors: Dominic J. Autelitano, Camberwell (AU); Michael C. Berndt, Mount Eliza (AU); Antonio Rajic, Reservoir (AU); A. Ian Smith, Hampton (AU); Gert Hoy Talbo, Viewbank (AU)

(73) Assignee: Healthlinx Limited, Victoria (AU)

( * ) Notice: Subject to any disclaimer, the term of this patent is extended or adjusted under 35 U.S.C. 154(b) by 497 days.

(21) Appl. No.: 10/897,068

(22) Filed: Jul. 23, 2004

(65) Prior Publication Data

US 2005/0208610 A1    Sep. 22, 2005

(30) Foreign Application Priority Data

Jul. 25, 2003    (AU) ............................... 2003903906

(51) Int. Cl.
*C07K 14/775*    (2006.01)

(52) U.S. Cl. ............................ 514/2; 514/12; 530/324; 530/380

(58) Field of Classification Search ....................... None
See application file for complete search history.

(56) References Cited

OTHER PUBLICATIONS

Lee et al. Dose-Response Study of Recombinant Factor VIIa/Tissue Factor Inhibitor Recombinant Nematode Anticoagulant Protein c2 in Prevention of Postoperative Venous Thromboemobolism in Patients Undergoing Total Knee Replacement. Circulation, 2001, pp. 74-78.*
Mahley, Robert et al.; Journal of Lipid Research, vol. 25, pp. 1277-1294 (1984).
McConathy, W. J. et al.; Journal of Lipid Research, vol. 33, pp. 995-1003 (1992).
Maeda, Nobuyo et al.,; The Journal of Biological Chemistry, vol. 269, No. 38, pp. 23610-23616 (1994).
Jong, Miek C. et al.; Arterioscler Throm Vas Biol., vol. 19, pp. 472-484 (1999).
Breslow, Jan L. , Proc. Natl. Acad. Sci. USA; vol. 90, pp. 8314-8318 (1993).
Sparrow, James T. et al.; Biochemistry, vol. 16, No. 25, pp. 5427-5431 (1977).
Sparrow, James T. et al.; CRC Critical Reviews in Biochemistry, vol. 13, Issue 1, pp. 88-107.
Ito, Yasushi et al.; Science, vol. 2, pp. 790-793 (1990.

* cited by examiner

*Primary Examiner*—Anish Gupta
(74) *Attorney, Agent, or Firm*—Birch, Stewart, Kolasch and Birch, LLP

(57) ABSTRACT

A method for producing an anticoagulation effect in a blood coagulation assay, said method comprising contacting a sample of blood with an effective amount of apolipoprotein CIII or fragment, derivative, homologue, analogue, chemical equivalent, functional equivalent or mimetic thereof.

5 Claims, 10 Drawing Sheets

Section of the MALDI-ISD-MS spectrum obtained from Apolipoprotein CIII. The shown spectrum covers the sequence from Ala[19] to Ser[29].

Chromogenic Substrate Assay for TF:VIIa mediated activation of Factor X

A.

B.

Effect of Apolipoprotein CIII fragment (amino acids 41-79) on Prothrombin Time in plasma from various species

Activity of Apolipoprotein CIII (amino acids 41-79) -derived peptides

SEQUENCE LISTING

```
<160> NUMBER OF SEQ ID NOS: 4

<210> SEQ ID NO 1
<211> LENGTH: 237
<212> TYPE: DNA
<213> ORGANISM: Homo sapiens

<400> SEQUENCE: 1
tcagaggccg aggatgcctc ccttctcagc ttcatgcagg gttacatgaa gcacgccacc        60
aagaccgcca aggatgcact gagcagcgtg caggagtccc aggtggccca gcaggccagg       120
ggctgggtga ccgatggctt cagttccctg aaagactact ggagcaccgt taaggacaag       180
ttctctgagt tctgggattt ggaccctgag gtcagaccaa cttcagccgt ggctgcc         237

<210> SEQ ID NO 2
<211> LENGTH: 79
<212> TYPE: PRT
<213> ORGANISM: Homo sapiens

<400> SEQUENCE: 2

Ser Glu Ala Glu Asp Ala Ser Leu Leu Ser Phe Met Gln Gly Tyr Met
1               5                   10                  15

Lys His Ala Thr Lys Thr Ala Lys Asp Ala Leu Ser Ser Val Gln Glu
                20                  25                  30

Ser Gln Val Ala Gln Ala Arg Gly Trp Val Thr Asp Gly Phe Ser
            35                  40                  45

Ser Leu Lys Asp Tyr Trp Ser Thr Val Lys Asp Lys Phe Ser Glu Phe
        50                  55                  60

Trp Asp Leu Asp Pro Glu Val Arg Pro Thr Ser Ala Val Ala Ala
65                  70                  75

<210> SEQ ID NO 3
<211> LENGTH: 117
<212> TYPE: DNA
<213> ORGANISM: Homo sapiens

<400> SEQUENCE: 3
ggctgggtga ccgatggctt cagttccctg aaagactact ggagcaccgt taaggacaag        60
ttctctgagt tctgggattt ggaccctgag gtcagaccaa cttcagccgt ggctgcc         117

<210> SEQ ID NO 4
<211> LENGTH: 39
<212> TYPE: PRT
<213> ORGANISM: Homo sapiens
```

```
<400> SEQUENCE: 4

Gly Trp Val Thr Asp Gly Phe Ser Ser Leu Lys Asp Tyr Trp Ser Thr
1               5                   10                  15

Val Lys Asp Lys Phe Ser Glu Phe Trp Asp Leu Asp Pro Glu Val Arg
            20                  25                  30

Pro Thr Ser Ala Val Ala Ala
            35
```

METHOD OF PRODUCING AN ANTICOAGULATION EFFECT

This Nonprovisional application claims priority under 35 U.S.C. § 119(a) on Patent Application No(s). 2003903906 filed in Australia on Jul. 25, 2003, the entire contents of which are hereby incorporated by reference.

FIELD OF THE INVENTION

The present invention relates generally to a method for producing an anticoagulation effect in a blood coagulation assay. The method of the present invention is useful in inter alia producing an anticoagulation effect in a subject and in the treatment and/or prophylaxis of conditions characterised by aberrant, unwanted or otherwise inappropriate blood coagulation in a subject.

BACKGROUND OF THE INVENTION

Bibliographic details numerically referred to in this specification are collected at the end of the description.

The reference to any prior art in this specification is not and should not be taken as, an acknowledgment or any form of suggestion that that prior art forms part of the common general knowledge in Australia.

Coagulation is an important mechanism in arresting bleeding and is a life-sustaining process. The two major arms of the blood coagulation cascade, the intrinsic and extrinsic pathways, consist of a series of stepwise, coordinated reactions involving specific plasma proteins in a process leading to thrombin generation which is in turn responsible for the conversion of fibrinogen to an impermeable cross-linked fibrin clot.

Blood coagulation or clotting takes place in three central phases. The first phase is the activation of a prothrombin activator complex. The second phase is the activation of prothrombin. The third stage is clot formation as a result of fibrinogen cleavage by activated thrombin.

The intrinsic and extrinsic pathways each lead to a different form of the prothrombin activator. The intrinsic mechanism of prothrombin activator formation begins with trauma to the blood or exposure of blood to collagen in a traumatised vessel wall. This usually also results in damage to fragile platelets. The cascade begins with the activation of factor XII (XIa) and the release of platelet factor 3 (PF3) from damaged platelets. Activated factor XII (requires prekallikrein and kininogen) cleaves and activates factor XI to become factor XIa. Activator factor XI converts factor IX to become activated factor IX (IXa) and factor IXa converts factor X to activated factor X (Xa). Calcium ions are required for the first three steps. Factor Xa then activates the common pathway of coagulation.

The extrinsic mechanism of prothrombin activator formation begins with trauma to vascular walls or extravascular tissues. The damaged tissue releases tissue thromboplastin also known as tissue factor (TF). The formation of a clot by this mechanism usually takes as little as 15 seconds. The cascade is initiated by the activation of factor X by TF and factor VII. Factor VIIa also activates factor IX in the presence of tissue factor, providing a connection between the "extrinsic" and "intrinsic" pathways. Factor Xa combined with factor V, factor VII and tissue factor constitutes the prothrombin activator. Calcium ions are required for each of these steps.

The common pathway of coagulation starts with the conversion of factor X to activated factor X described in the above paragraphs by the intrinsic and extrinsic pathways. Activated factor X requires its own cofactors for activity, including calcium ions, circulating factor V and an electrically charged platelet surface for localisation. It is then able to cleave prothrombin to produce activated thrombin. Thrombin converts fibrinogen (soluble) to fibrin (insoluble) and activates factor VIII. A network of insoluble fibrin (stabilised by thrombin) is formed, which is localised to the site of injury and traps oncoming blood platelets and plasma to form a clot.

The physiological function of coagulation is to prevent the loss of blood after injury and is part of a mechanism called haemostasis which is the result of a complex balance between the processes of fibrin clot initiation, formation and dissolution. However, certain events such as damage to the vessel wall or changes in blood flow can upset the balance and produce changes in the processes of coagulation that result in abnormal clot formation (thrombosis) in blood vessels.

Thrombosis is a pathological process in which a platelet aggregate and/or fibrin clot forms in the lumen of an intact blood vessel or in a chamber of the heart. If thrombosis occurs in an artery, myocardial infarction and unstable angina may result as a result of the tissue supplied by the artery undergoing ischaemic necrosis. Thrombosis formation in venous vasculature may result in a pulmonary embolism due to reduced blood flow. Disseminated intravascular coagulopathy in both the venous and arterial systems commonly occurs during septic shock, some viral infections and cancer which often leads to rapid and widespread thrombus formation and organ failure.

Current anticoagulant therapies such as heparin and warfarin, while effective, have several limitations such as an elevated risk of bleeding and inconvenience posed by the need for routine coagulation monitoring and/or parenteral administration. Heparin for example, is limited by the requirement for parenteral administration, constant monitoring, narrow therapeutic window, heparin rebound, thrombocytopaenia and bleeding. Warfarin, similarly, can lead to bleeding and may require constant monitoring due to its narrow therapeutic range and somewhat unpredictable effect. Thus, there is still a need to develop compounds or substances which have improved efficacy, safety and ease of use.

Human apolipoprotein CIII is a 8.8 kD protein glycosylated at $Thr^{74}$ and synthesized in the liver and intestine. It is part of the apolipoprotein C family which also includes apolipoprotein CI and apolipoprotein CII. Apolipoprotein CIII plays a central role in modulating metabolism of triglyceride-rich plasma lipoproteins and levels in normal human plasma are 100-150 μg/ml. It is associated predominantly with triglyceride-rich very low density lipoprotein (VLDL). Some apolipoprotein CIII are associated with high density lipoprotein (HDL). In man, plasma triglyceride levels are positively associated with apolipoprotein CIII levels. Transgenic overexpression in mice results in hypertriglyceridemia (Ito Y., Science, 249: 790-793, 1990). Apolipoprotein CIII gene knockout mice are hypotriglyceridemic (Maeda N. et al., J. Biol. Chem., 269: 23610-23616, 1994). Apolipoprotein CIII inhibits lipoprotein lipase activity and reduces uptake and clearance of triglyceride-rich lipoproteins by the liver. Taken together, there is strong evidence that increased plasma levels of apolipoprotein CIII contribute to the development of hypertriglyceridemia in man (for review, see; Mahley, R. W. et al., J. Lipid Res., 25: 1277, 1984; Jong, M. C. et al., Arterioscler. Thromb. Vasc. Biol., 19: 472, 1999; Breslow, J. Proc. Natl. Acad. Sci., USA, 90:8314, 1993). Human apolipoprotein CIII exists in three forms depending upon the level of sialylation: $C\text{-}III_0$, $C\text{-}III_1$, and $C\text{-}III_2$. The subscript indicates the number of sialic acid residues, however, the $C\text{-}III_0$ form does not include the neutral carbohydrates. Glycosylation occurs on threonine (T) at position 74.

Several human apolipoprotein CIII polymorphisms have been described. Thrombin cleavage of apolipoprotein CIII into two fragments, 1-40 and 41-79 suggests that the C-terminal 41-79 peptide can bind phospholipid (Sparrow J. T. et al., Biochemistry 16:5427-31, 1977). Synthetic apolipoprotein CIII peptides suggest that the minimal sequence required for phospholipid binding is contained within amino acids 48-79 (Sparrow J. T. and Gotto A. M., CRC Crit. Rev. Biochem. 13: 87-107, 1982). Inhibition of lipoprotein lipase activity is mediated by the N-terminal domain of apolipoprotein CIII (McConathy W. J. et al., J. Lipid Res. 33: 995-1003, 1992).

In work leading up to the present invention, the inventors determined that a fragment of apolipoprotein CIII (SEQ ID NO: 2), being a polypeptide comprised of amino acids 41-79 (SEQ ID NO: 4) prolonged induction of blood coagulation in in vitro prothrombin time assays. Such results indicate that the fragment of apolipoprotein CIII is capable of inhibiting blood coagulation by inhibiting the extrinsic coagulation pathway.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). A summary of the sequence identifiers is provided in Table 1.

One aspect of the present invention provides a method for producing an anticoagulation effect in a blood coagulation assay, said method comprising contacting a sample of blood with an effective amount of apolipoprotein CIII or fragment, derivative, homologue, analogue, chemical equivalent, functional equivalent or mimetic thereof.

Another aspect of the present invention provides a method for producing an anticoagulation effect in a subject, said method comprising administering to said subject, an effective amount of apolipoprotein CIII or fragment, derivative, homologue, analogue, chemical equivalent, functional equivalent or mimetic thereof.

Still yet another aspect provides a method for the prophylactic and/or therapeutic treatment of a condition characterised by the aberrant, unwanted or otherwise inappropriate blood coagulation in a subject, said method comprising administering to said subject, an effective amount of a composition comprising apolipoprotein CIII or fragment, derivative, homologue, analogue, chemical equivalent, functional equivalent or mimetic thereof.

Conditions characterised by aberrant, unwanted, or otherwise inappropriate blood coagulation including haemostasis related disorders; hypercoagulate states, including inherited or acquired; thrombosis including deep vein thrombosis; pulmonary embolism; thromboembolic complications associated with atrial fibrillation; cardiac valve replacement; percutaneous transluminal angioplasty; ischemia-reperfusion injury and post-operative thromboembolism.

A preferred apolipoprotein CIII fragment or derivative is the lipid binding fragment of apolipoprotein CIII, even more preferably a polypeptide comprising amino acids 41-79 thereof (SEQ ID NO: 4). Without wishing to limit the invention to one mechanism of action, it is proposed that the lipid binding fragment of apolipoprotein CIII, or at least a polypeptide comprising amino acids 41-79 thereof, interacts with the tissue factor: VIIa complex thereby inhibiting the extrinsic coagulation pathway.

In the method of the present invention, the apolipoprotein CIII or fragment, derivative, homologue, analogue, chemical equivalent, functional equivalent or mimetic thereof may be administered orally (including buccal, sublingual, inhalation), nasally, rectally, vaginally, intravenously (including intrarterially), intradermally, subcutaneously, intramuscularly and topically.

The apolipoprotein CIII or fragment, derivative, homologue, analogue, chemical equivalent, functional equivalent or mimetic thereof may be administered to a subject in a composition which may also include additional active ingredients in particular additional anticoagulants (eg. aspirin, warfarin, heparin) and/or thrombolytic agents (eg. streptokinase, tPA, TNKase.™).

Alternatively, targeting therapies may be used to deliver the apolipoprotein CIII or fragment, derivative, homologue, analogue, chemical equivalent, functional equivalent or mimetic thereof more specifically to certain types of cell, by the use of targeting systems such as antibodies or cell specific ligands or specific nucleic genetic material.

In yet another alternative, stem cells may be isolated, genetically modified to produce the apolipoprotein CIII or fragment, derivative, homologue, analogue, chemical equivalent, functional equivalent or mimetic thereof (constitutively or developmentally) with the cell culture in vivo or ex vivo for regeneration, augmentation or tissue repair therapy.

The method of the present invention also includes providing a nucleotide sequence encoding apolipoprotein CIII or fragment, derivative, homologue, analogue, chemical equivalent, functional equivalent or mimetic thereof to a cell.

In another aspect there is provided a method for producing an anticoagulation effect in a sample of blood, said method comprising introducing to said sample of blood, an effective amount of apolipoprotein CIII or fragment, derivative, homologue, analogue, chemical equivalent, functional equivalent or mimetic thereof.

In another embodiment, a nucleotide sequence encoding apolipoprotein CIII or fragment, derivative, homologue, analogue, chemical equivalent, functional equivalent or mimetic thereof is administered to an animal or human subject.

A summary of sequence identifiers used throughout the subject specification is provided in Table 1.

TABLE 1

Summary of sequence identifiers

| SEQUENCE ID NO: | DESCRIPTION |
|---|---|
| 1 | apolipoprotein CIII nucleotide sequence encoding mature apolipoprotein CIII polypeptide<br>tcagaggccgaggatgcctcccttctcagcttcatgcagggttacatgaagcacgccaccaa gaccgccaaggatgcactgagcagcgtgcaggagtcccaggtggcccagcaggccaggggct gggtgaccgatggcttcagttccctgaaagactactggagcaccgttaaggacaagttctct |

TABLE 1-continued

Summary of sequence identifiers

| SEQUENCE ID NO: | DESCRIPTION |
|---|---|
| | gagttctgggatttggaccctgaggtcagaccaacttcagccgtggctgcc |
| 2 | mature apolipoprotein CIII polypeptide amino acid sequence<br>SEAEDASLLSFMQGYMKHATKTAKDALSSVQESQVAQQARGWVTDGFSSLKDYWSTVKDKFS<br>EFWDLDPEVRPTSAVAA |
| 3 | nucleotide sequence encoding amino acids 41-79 of SEQ ID NO: 2<br>ggctgggtgaccgatggcttcagttccctgaaagactactggagcaccgttaaggacaagtt<br>ctctgagttctgggatttggaccctgaggtcagaccaacttcagccgtggctgcc |
| 4 | amino acid residues 41-79 of SEQ ID NO: 2<br>GWVTDGFSSLKDYWSTVKDKFSEFWDLDPEVRPTSAVAA |

A) A human plasma fraction resulting from precipitation with 1 volume of acetontrile was chromatographically separated by Reversed Phase-HPLC using a Zorbax 300SB-C18 column (5 mm, 4.6×250 mm) using a linear gradient of 0-70% solvent B over 30 mins at a flow rate of 1 ml/min. Solvent A consisted of 0.1% trifluoroacetic acid (TFA) in milli-Q $H_2O$ and solvent B consisted of 0.08% TFA in acetonitrile. Fractions were collected at 1 minute intervals directly into 96 well polypropylene library plates, lyophilized and reconstituted in 75 µl $NH_4HCO_3$. Screening of fractions with a high throughput prothrombin time (PT) coagulation assay demonstrated the presence of a PT inhibitory factor eluting predominantly in fraction 41, with lower activity in fraction 40. B) The major inhibitory fraction (#41) from A) was subjected to a second chromatographic step by Reversed Phase-HPLC using a Zorbax 300SB-C18 column (5 mm, 2.1×150 mm) using a linear gradient of 0-100% solvent B over 91 mins at a flow rate of 0.5 ml/min. Solvent A consisted of 10 mM $NH_4HCO_3$ in milli-Q $H_2O$, pH 8 and solvent B consisted of 10 mM $NH_4HCO_3$ in 70% acetonitrile, pH 8. Screening of fractions with a high throughput prothrombin time (PT) coagulation assay demonstrated that fractions 53-55 all led to prolonged prothrombin times, with fraction 54 having the greatest inhibitory effect. C) Positive ion MALDI mass spectrum of apolipoprotein C-III in its various isoforms depending on the number of post-translational sialic acids added. Apolipoprotein CIII with 0, 1 and 2 sialic acids attached corresponds to apoC-$III_0$, apoC-$III_1$ and apoC-$III_2$.

Figure 2:
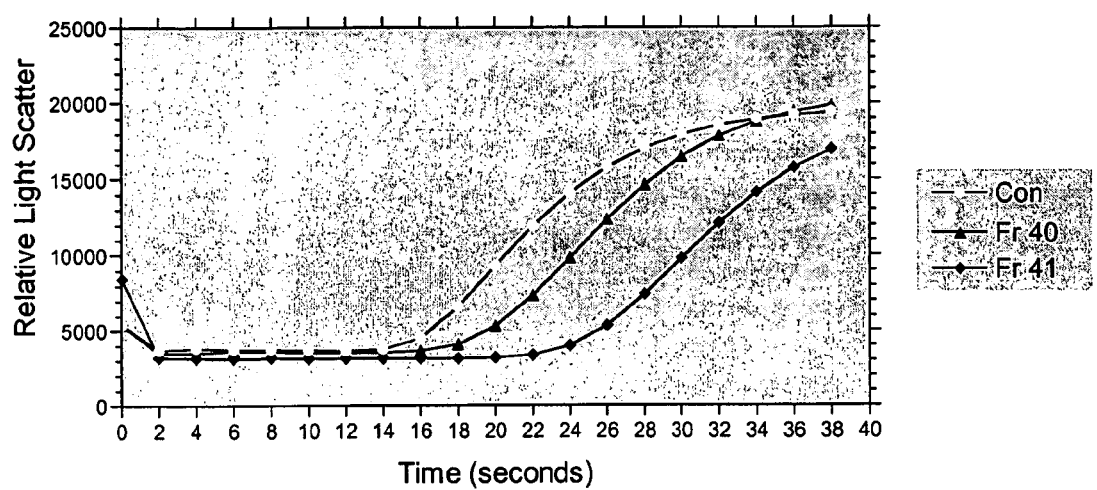

FIG. 2. Prothrombin time (PT) coagulation as determined by a high throughput, nephelometric-based method in microwell plates.

Automated laser-based nephelometry of each well sensitively detects time-dependent induction of coagulation as an increase in relative light scatter. A soluble human plasma fraction obtained following precipitation with 1 volume of acetonitrile was separated by RP-HPLC to produce the initial library. Two fractions (40, 41) led to a delayed PT response when pre-incubated with platelet poor plasma (PPP) for 5 minutes prior to initiating coagulation with a commercial thromboplastin reagent. The control prothrombin time of 16 seconds was extended to 18 seconds by Fr 40 and to 24 seconds by Fr 41.

Figure 3:
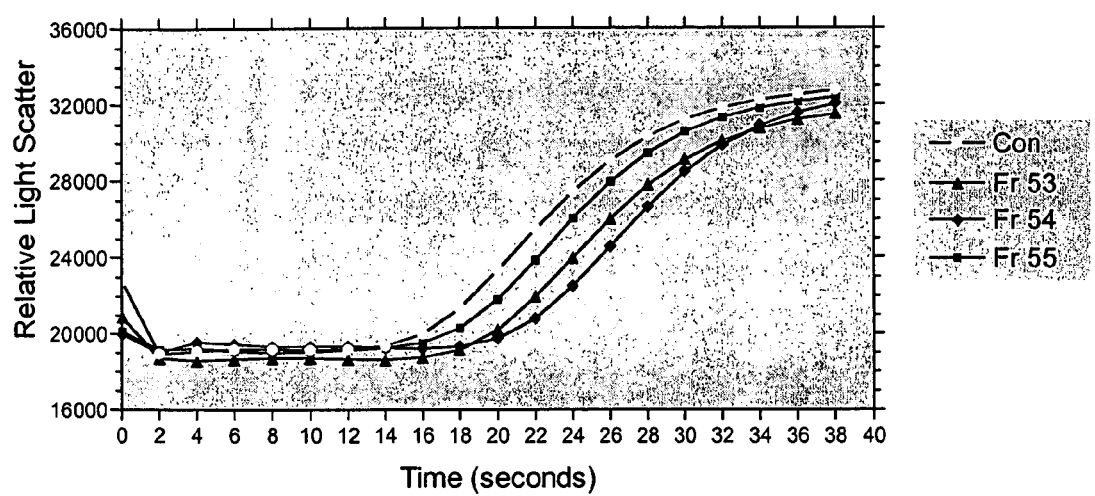

FIG. 3. Prothrombin time (PT) coagulation as determined by a high throughput, nephelometric-based method in microwell plates.

Automated laser-based nephelometry was used to detect time-dependent induction of coagulation as an increase in relative light scatter. The major inhibitory fraction (#41; see FIG. 2) was subjected to a second chromatographic step by Reversed Phase-HPLC using a Zorbax 300SB-C18 column (5 mm, 2.1×150 mm) using a linear gradient of 0-100% solvent B over 91 mins at a flow rate of 0.5 ml/min. Solvent A consisted of 10 mM $NH_4HCO_3$ in milli-Q $H_2O$, pH 8 and solvent B consisted of 10 mM $NH_4HCO_3$ in 70% acetonitrile, pH 8. Screening of fractions with a high throughput prothrombin time (PT) coagulation assay demonstrated that fractions 53-55 all led to prolonged prothrombin times, with fraction 54 having the greatest inhibitory effect.

Figure 4:
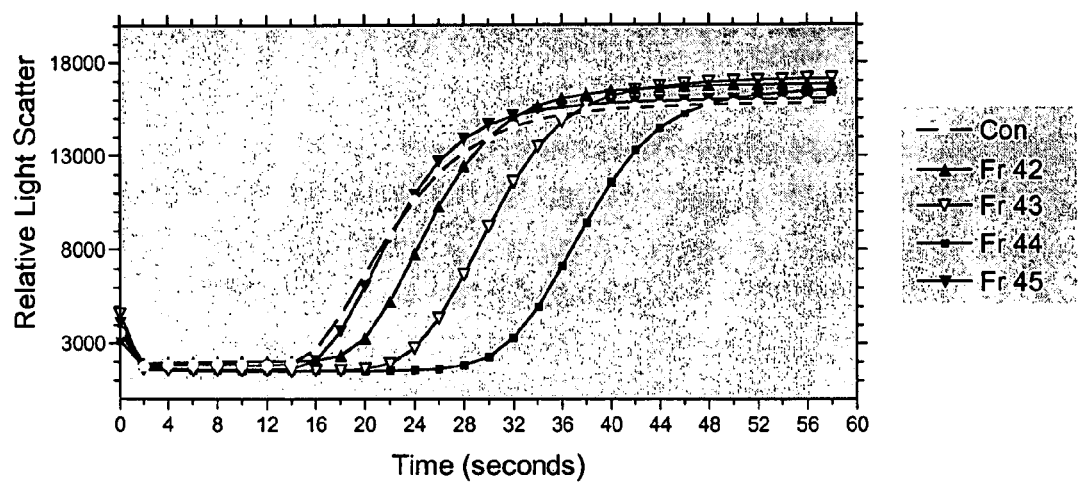

FIG. 4. Prothrombin time (PT) coagulation activity of a apolipoprotein CIII tryptic digest.

Tryptic digestion of apolipoprotein CIII was carried out in 25 mM $NH_4HCO_3$, 10% acetonitrile, pH 8 at 37° C. for 2 hours and was monitored by MALDI-MS prior to fractionation by RP-HPLC. The tryptic digest was then separated by reversed phase chromatography on a Zorbax 300SB-C18 column (2.1×150 mm) using a linear gradient of 0-100% solvent B over 91 mins at a flow rate of 0.5 ml/min. Solvent A consisted of 10 mM $NH_4HCO_3$ in milli-Q $H_2O$, pH 8 and solvent B consisted of 10 mM $NH_4HCO_3$ in 70% acetonitrile, pH 8. Screening of fractions with a high throughput prothrombin time (PT) coagulation assay demonstrated that fractions 42-46 all led to prolonged prothrombin times, with fraction 44 having the greatest inhibitory effect. MALDI-MS analysis demonstrated that fraction 44 predominantly contained the apolipoprotein $CIII_1$, (41-79) peptide.

Figure 5:
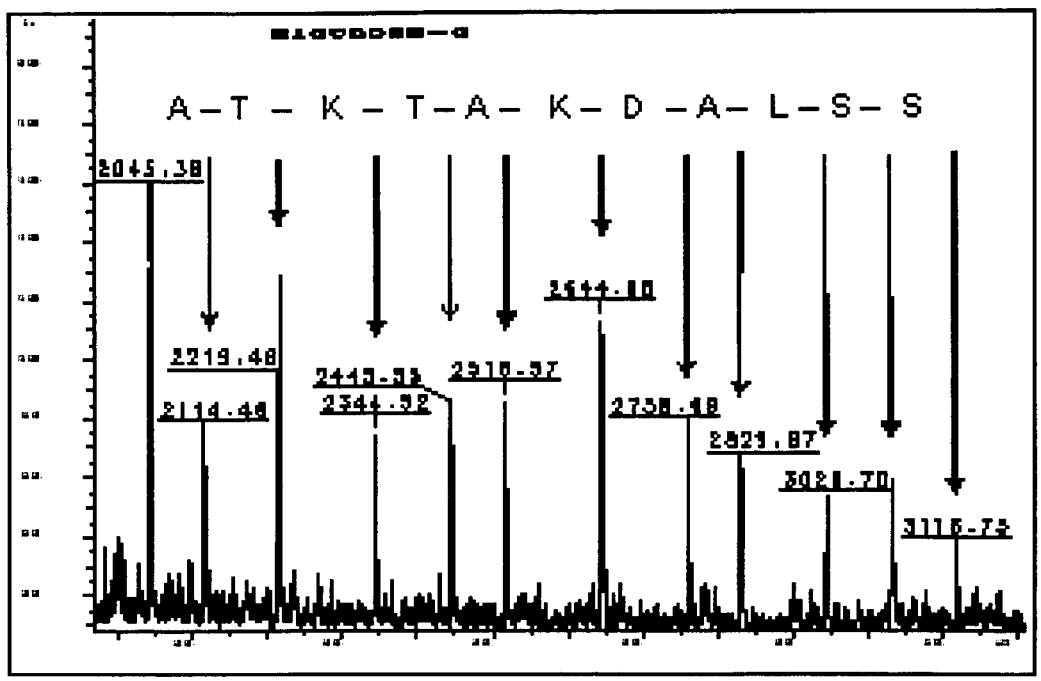

FIG. 5. Section of the MALDI-ISD -MS spectrum obtained from Apolipoprotein CIII.

The spectrum shown covers the sequence from $Ala^{19}$ to $Ser^{29}$.

Figure 6:
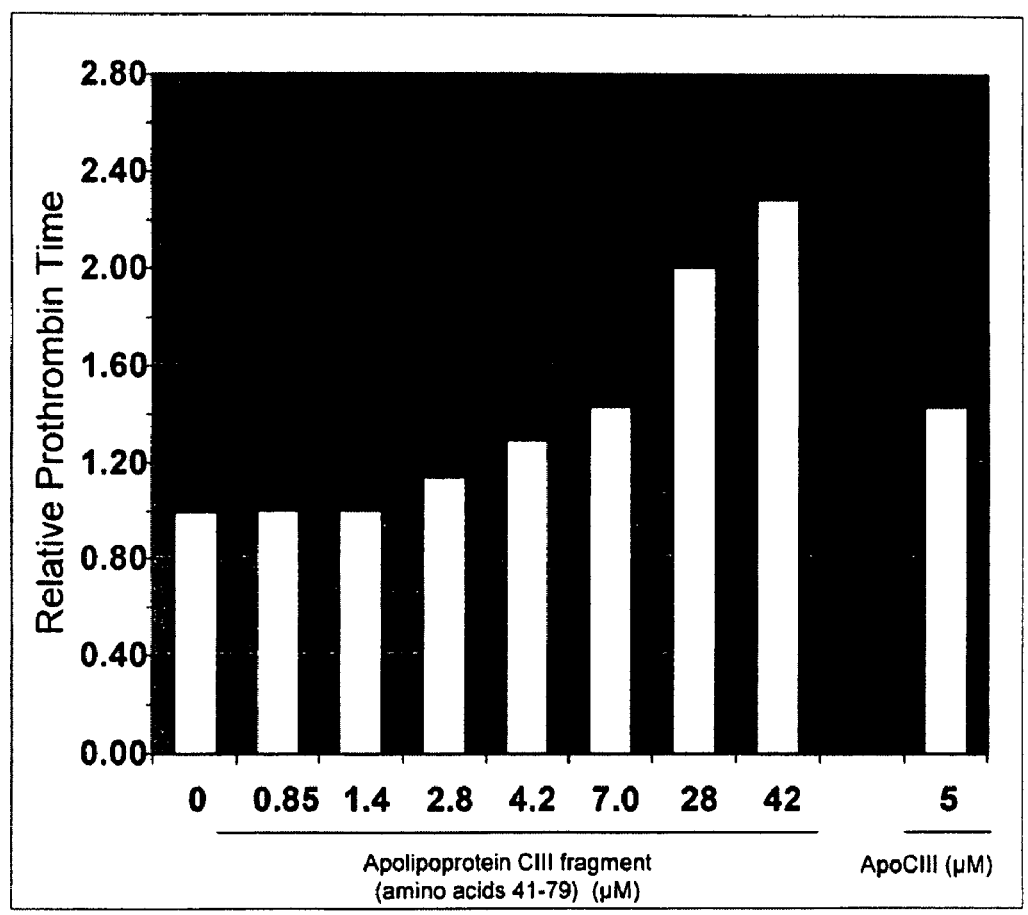

FIG. 6. Prothrombin time of citrated human plasma.

FIG. 6 is a graph showing concentration of Apolipoprotein CIII fragment (amino acids 41-79) versus relative prothrombin time.

Figure 7:
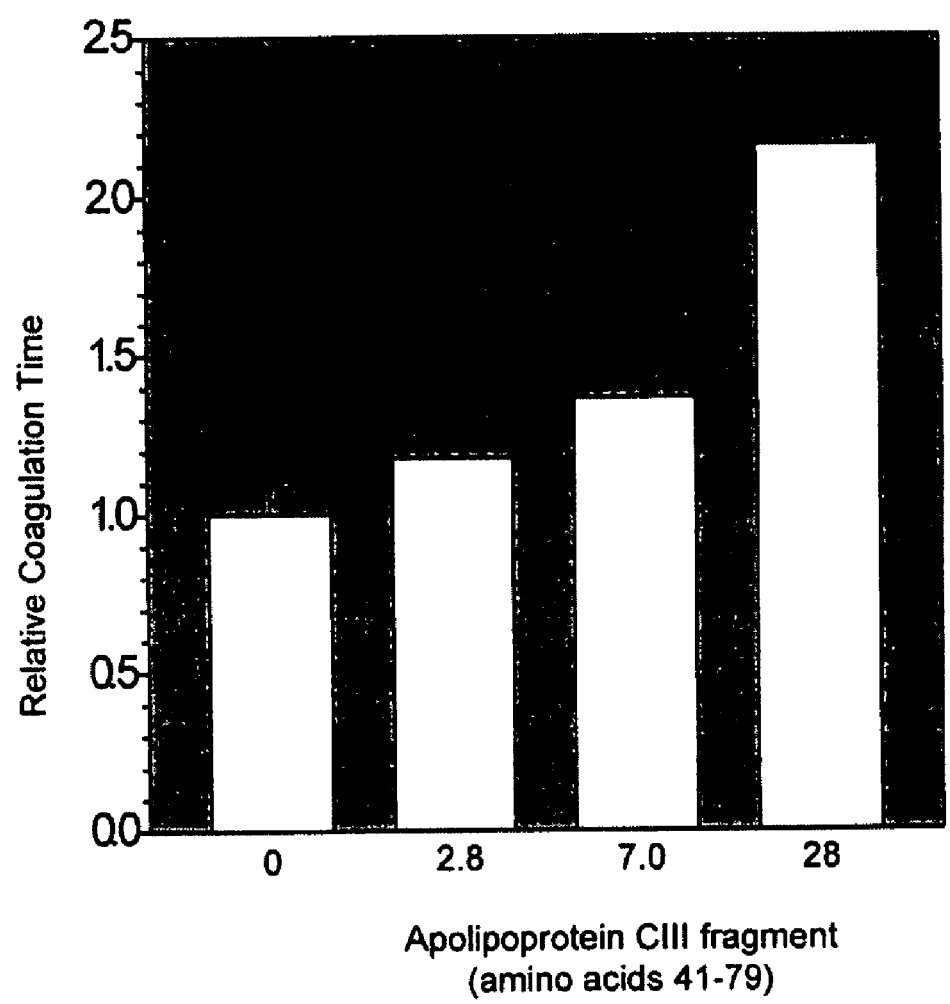

FIG. 7. TF-mediated coagulation in whole human blood.

FIG. 7 is a graph showing concentration of Apolipoprotein CIII fragment (amino acids 41-79) versus relative coagulation time.

Figure 8:
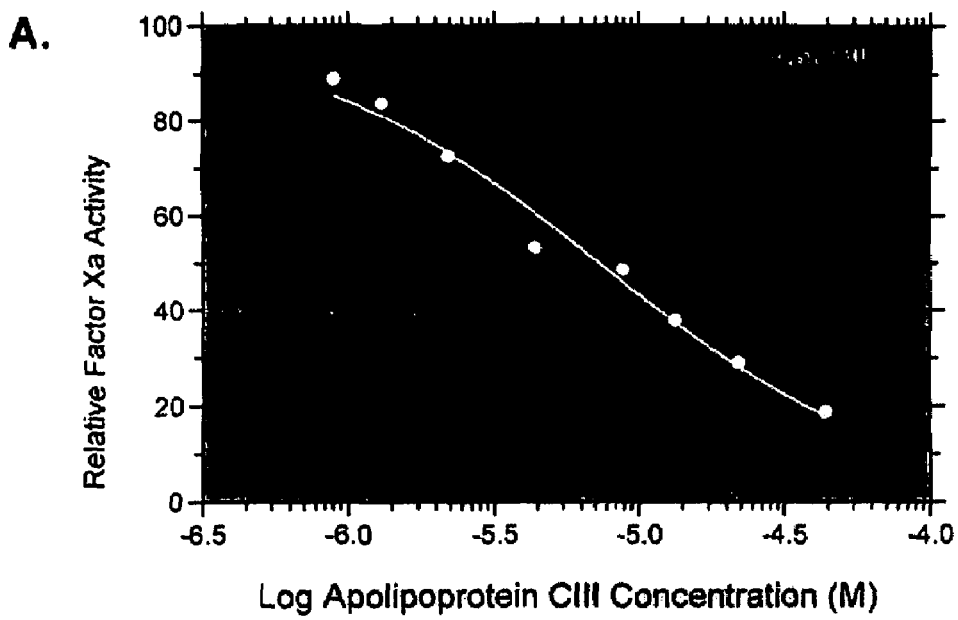
Figure 8:
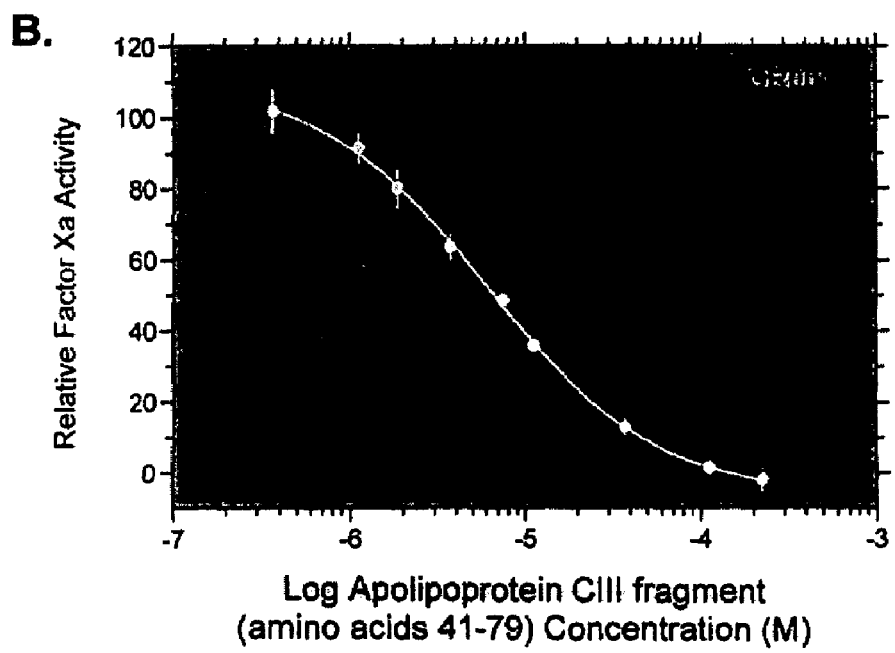

FIG. 8. Chromogenic Substrate Assay for TF:VIIa mediated activation of Factor X.

FIG. 8A is a graph showing log Apolipoprotein CIII concentration versus relative factor Xa activity.

FIG. 8B is a graph showing log ApolipoproteinCIII fragment (amino acids 41-79) concentration versus relative Xa activity.

Figure 9:
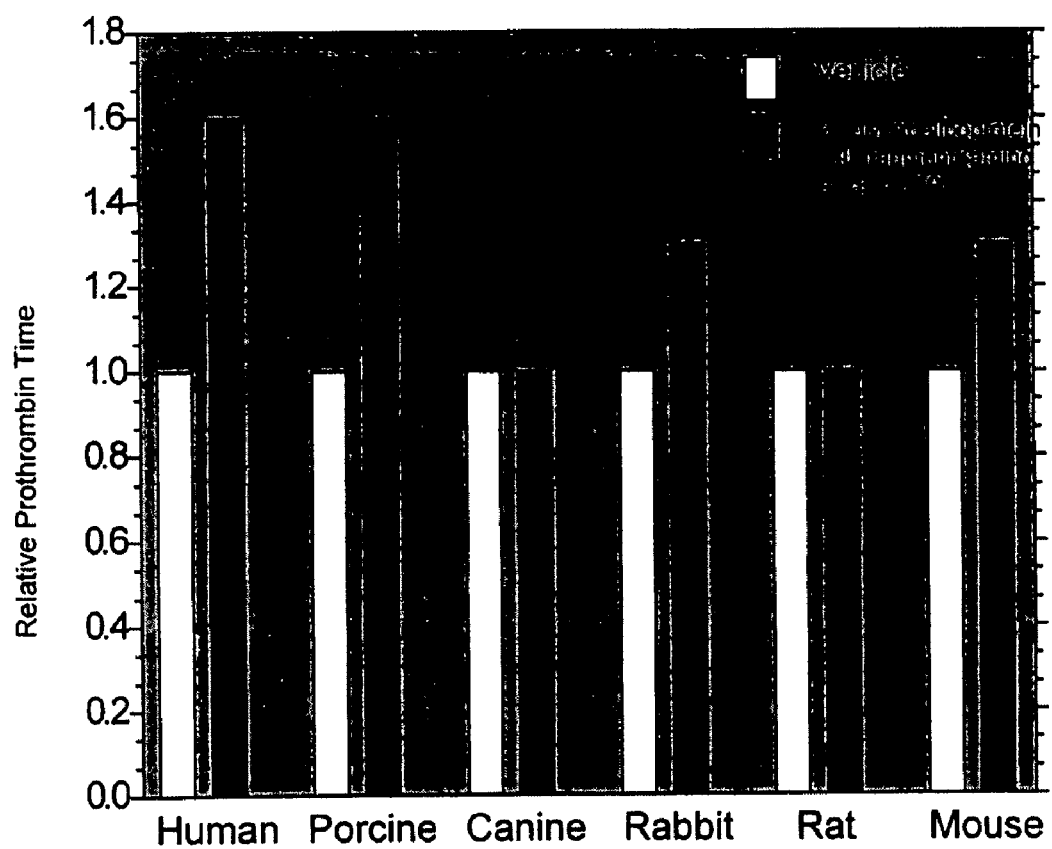

FIG. 9. Effect of Apolipoprotein CIII fragments (amino acids 41-79) on prothrombin time in plasma from various species.

FIG. 9 shows the effect of a single concentration of Apolipoprotein CIII fragment (amino acids 41-79) (22 µM) on relative prothrombin time in human, porcine, canine, rabbit, rat and mouse.

Figure 10:
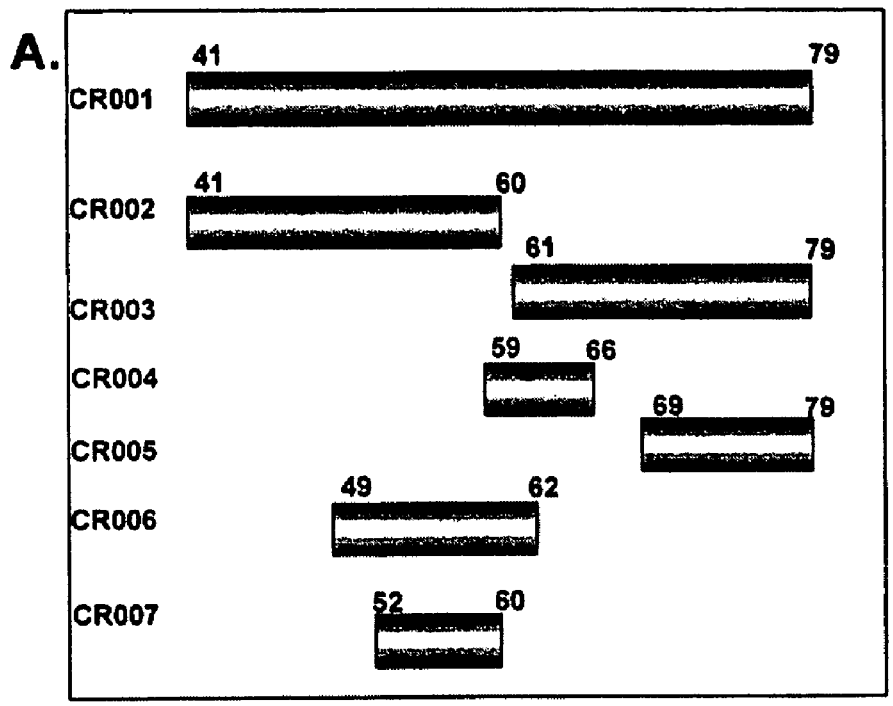
Figure 10:
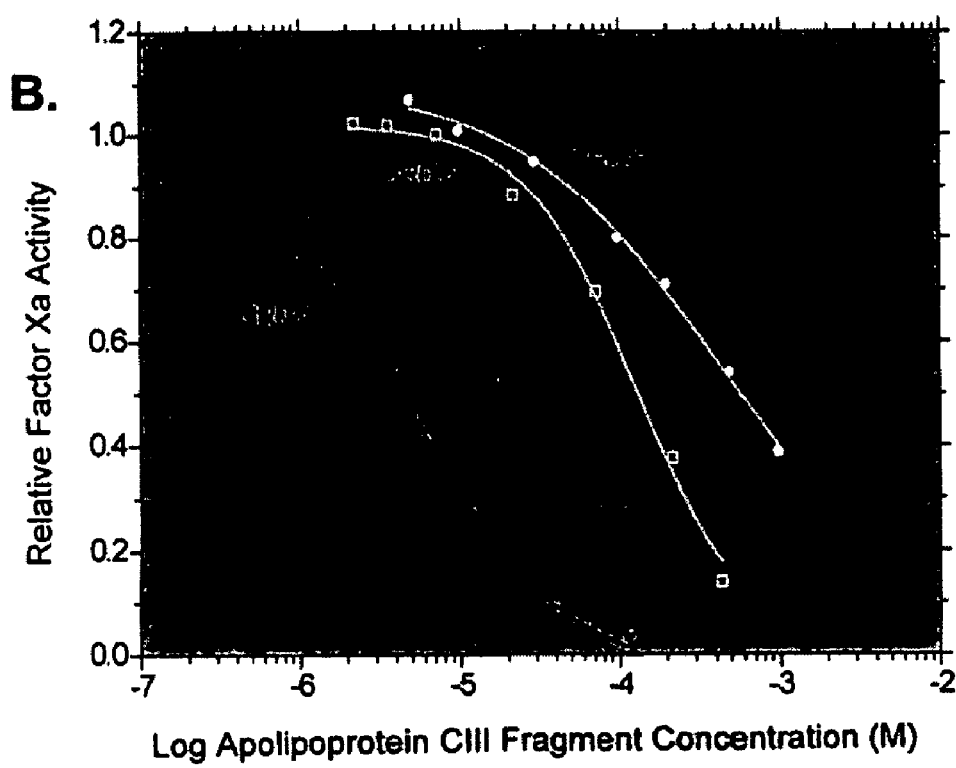

FIG. 10. Activity of Apolipoprotein CIII fragment (amino acids 41-79) derived peptides.

FIG. 10A shows a variety of Apolipoprotein CIII fragment (amino acids 41-79)-derived peptides.

FIG. 10B is a graph showing log Apolipoprotein CIII fragment-derived peptides (amino acids 41-60 and amino acids 49-62) concentration versus relative factor Xa activity.

DETAILED DESCRIPTION OF THE INVENTION

Before describing the present invention in detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting. It must be noted that, as used in the subject specification, the singular forms "a", "an" and "the" include plural aspects unless the context clearly dictates otherwise.

The present invention is predicated, in part, on the determination that apolipoprotein CIII maintains inhibitory activity on prothrombin assays. Without wishing to limit the theory of the present invention, it is believed that a fragment of apolipoprotein CIII being the polypeptide comprising amino acids 41-79 disclosed in SEQ ID NO: 4 interacts with thromboplastin and prolongs prothrombin time, by inhibiting the extrinsic pathway.

Accordingly, one aspect of the present invention provides a method for producing an anticoagulation effect in a blood coagulation assay, said method comprising contacting a sample of blood with an effective amount of apolipoprotein CIII or fragment, derivative, homologue, analogue, chemical equivalent, functional equivalent or mimetic thereof.

The term "anticoagulation effect" is used to refer to the effect of prevention or inhibition or prolonging of blood coagulation in an in vitro or in vivo assay of blood coagulation, or in a sample of blood, or in a subject. Blood coagulation assays are known in the art and include, but are not limited to, for example prothrombin time assays.

The prothrombin time and international normalised ratio are ways of measuring the extrinsic system in the coagulation pathway—factors II, VII and X. Thromboplastin and plasma are mixed at 37° C. and the time taken for a clot to form after the addition of calcium is measured; this is the prothrombin time. The time to clot is compared to a control—this is the international normalised ratio (INR). The normal range of INR is 0.9 to 1.2.

The anticoagulant effect achieved by the method of the present invention is enhanced, by its ability to prevent, or inhibit or prolong blood coagulation, surpassing the ability of a standard in vivo or in vitro assay of blood coagulation, such as the assays referred to above. In the present invention the prothrombin time is one method of measuring the anticoagulation effect of administering an effective amount of apolipoprotein CIII or fragment, derivative, homologue, analogue, chemical equivalent, functional equivalent or mimetic thereof to a sample of blood or to a subject. Preferably, the difference between the anticoagulation effect achieved within the scope of the present invention and a reference prothrombin assay is at least about 5%, more preferably at least about 10%, even more preferably at least about 25%, even more preferably at least about 50%, most preferably at least about 90% as determined by side-by-side comparison in a selected control blood coagulation assay.

Reference to "sample" should be understood as a reference to any sample of biological material derived from an animal such, but not limited to, mucus, faeces, urine, biopsy specimens and fluid which has been introduced into the body of an animal and subsequently removed such as, for example, the saline solution extracted from the lung following lung lavage or the solution retrieved from an enema wash. The sample which is tested according to the method of the present invention may be tested directly or may require some form of treatment prior to testing. For example, a biopsy sample may require homogenisation prior to testing. Further, to the extent that the biological sample is not in liquid form, (for example it may be a solid, semi-solid or a dehydrated liquid sample) it may require the addition of a reagent, such as a buffer, to mobilise the sample.

The term "blood" is understood to mean whole blood; however blood also can be any fraction thereof, for example plasma, packed cells, buffy coat and a concentrated suspension of cells.

Another aspect of the present invention provides a method for producing an anticoagulation effect in a subject, said method comprising administering to said subject, an effective amount of apolipoprotein CIII or fragment, derivative, homologue, analogue, chemical equivalent, functional equivalent or mimetic thereof.

Still yet another aspect provides a method for the prophylactic and/or therapeutic treatment of a condition characterised by the aberrant, unwanted or otherwise inappropriate blood coagulation in a subject, said method comprising administering to said subject, an effective amount of a composition comprising apolipoprotein CIII or fragment, derivative, homologue, analogue, chemical equivalent, functional equivalent or mimetic thereof.

Reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition. Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

Conditions characterised by aberrant, unwanted, or otherwise inappropriate blood coagulation including haemostasis related disorders, thrombosis including deep vein thrombosis; pulmonary embolism, thromboembolic complications associated with atrial fibrillation, cardiac valve replacement, percutaneous transluminal angioplasty, ischemia-reperfusion injury, post-operative thromboembolism, and hypercoagulate states. Hypercoagulability may be defined as a state in which there is a risk of thrombosis in circumstances which would not usually cause thrombosis in the normal individual. Hypercoagulate states may be inherited or acquired. Inherited hypercoagulable states are an inherited tendency to thrombosis and is termed thrombophilia. In many cases specific prothrombic mutations in antithrombotic factors are responsible. Acquired coagulation disorders including disseminated intravascular coagulation (which is a condition where the physiological generation of thrombin becomes unregulated) are usually acquired during life usually in an individual who is unwell or immobile.

The common causes of a secondary or acquired hypercoagulable state fall into three main categories:
1. venous stasis caused by:
   immobility
   obesity
   congestive cardiac failure
   post-operative bedrest
2. coagulation factor activation caused by:
   malignant disease
   pregnancy
   oestrogen and oral contraceptive use
   nephrotic syndrome
   antiphospholipid syndrome
3. platelet activation caused by:
   myeloproliferative disorders
   thrombotic thrombocytopenic purpura Commonly, an acute thrombotic episode results in an individual who acquires a hypercoagulable state on the background of a primary or inherited hypercoagulability.

A "subject" is a mammal and includes, humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Preferably, the mammal is a human. Although the present invention is exemplified herein with respect to laboratory test animals, this should not be understood in any way as limiting the application of the present invention to humans.

Reference to "apolipoprotein CIII" should be understood as a reference to all forms of, apolipoprotein CIII, and to the extent that it is not specified, to fragments, derivatives, homologues, analogues, chemical equivalents or mimetics thereof. This includes, for example, all protein forms of this molecule or its functional equivalents or derivatives including, for example, any isoforms which may arise from alternative splicing of the encoding mRNA. It includes reference to mutants, polymorphic variants or homologues of this molecule. It also includes reference to analogues or equivalents of this molecule. For example, human apolipoprotein CIII exists in three forms depending on the level of sialylation: $C-III_0$, $C-III_1$ and $C-III_2$. The subscript indicates the number of sialic acid residues, however, the $C-III_0$ form does not include the neutral carbohydrates. Reference to "apolipoprotein CIII" should also be understood to include reference to genetic molecules encoding apolipoprotein CIII or to derivatives, homologues or analogues of said nucleic acid molecules.

"Derivatives" include fragments, parts, portions, mutants, variants and mimetics from natural, synthetic or recombinant sources, including fusion proteins. Parts or fragments include, for example, active regions of apolipoprotein CIII. Preferably, such fragments include the lipid binding fragment or portion of apolipoprotein CIII, particularly the polypeptide disclosed in SEQ ID NO: 4. As used herein, fragment means an amino acid or nucleotide sequence that comprises at least about 10% or more of the parent amino acid or nucleotide sequence. For example, the fragment of apolipoprotein CIII may comprise 10% or more of the amino acid sequence of apolipoprotein CIII (SEQ ID NO:2) or 10% or more of the nucleotide sequence encoding apolipoprotein CIII (SEQ ID NO:1). Examples of fragments include molecules comprising at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% of the parent amino acid sequence (SEQ ID NO: 2).

Examples of fragments also include molecules comprising amino acids 2-79, 3-79, 4-79, 5-79, 6-79, 7-79, 8-79, 9-79, 10-79, 11-79, 12-79, 13-79, 14-79, 15-79, 16-79, 17-9, 18-79, 19-79, 20-79, 21-79, 22-79, 23-79, 24-79, 25-79, 26-79, 27-79, 28-79, 29-79, 30-79, 31-79, 32-79, 33-79, 34-79, 35-79, 36-79, 37-79, 38-79, 39-79, 40-79, and 41-79 of the amino acid sequence disclosed in SEQ ID NO:2.

Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences including fusions with other peptides, polypeptides or proteins.

A "conservative substitution" is one in which an amino acid is substituted for another amino acid that has similar properties, such that one skilled in the art of peptide chemistry would expect the secondary structure and hydropathic nature of the apolipoprotein CIII apolipoprotein CIII or fragment, derivative, homologue, analogue, chemical equivalent, functional equivalent or mimetic thereof to be substantially unchanged. When it is desired to alter the amino acid sequence of apolipoprotein CIII or fragment, derivative, homologue, analogue, chemical equivalent, functional equivalent or mimetic thereof to create an altered protein, one skilled in the art will typically change one or more amino acids.

For example, certain amino acids may be substituted for other amino acids in the apolipoprotein CIII or fragment, derivative, homologue, analogue, chemical equivalent, functional equivalent or mimetic thereof sequence without appreciable loss of the protein's activity. Since it is the interactive capacity and nature of a protein that defines that protein's biological functional activity, certain amino acid sequence substitutions can be made in the apolipoprotein CIII or fragment, derivative, homologue, analogue, chemical equivalent, functional equivalent or mimetic's thereof protein sequence, and, of course, its underlying DNA coding sequence, and nevertheless obtain a protein with like properties. Alternatively, substitutions may be made which either enhance or diminish the desired properties of the apolipoprotein CIII or fragment, derivative, homologue, analogue, chemical equivalent, functional equivalent or mimetic thereof. It is thus contemplated that various changes may be made in the peptide sequences of the apolipoprotein CIII or fragment, derivative, homologue, analogue, chemical equivalent, functional equivalent or mimetic thereof, or corresponding DNA sequences which encode apolipoprotein CIII or fragment, derivative, homologue, analogue, chemical equivalent, functional equivalent or mimetic thereof without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, *Journal of Molecular Biology* 157(1): 105-132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982, supra). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). Based on the hydropathic index, amino acids can be divided into the following four groups:
1. polar, but uncharged R groups: serine, threonine, asparagine, tyrosine and glutamine;
2. acidic side chains: aspartic acid and glutamic acid;
3. basic side chains: lysine, arginine and histidine; and
4. non-polar side chains: glycine, alanine, valine, leucine, isoleucine, proline, phenylalanine, methionine, tryptophan and cysteine.

It is known in the art that amino acids within a given group may be substituted by another amino acids from the same group based on a similar hydropathic index or score and still result in a protein with similar biological activity, i.e. still obtain a biological functionally equivalent protein.

Chemical and functional equivalents of the apolipoprotein CIII or fragment, derivative, homologue, analogue, chemical equivalent, functional equivalent or mimetic thereof or its encoding nucleic acid molecule should be understood as molecules exhibiting any one or more of the functional activities of these molecules and may be derived from any source such as being chemically synthesized or identified via screening processes such as natural product screening.

The derivatives of apolipoprotein CIII or fragment, derivative, homologue, analogue, chemical equivalent, functional equivalent or mimetic thereof include fragments having particular epitopes or parts of the entire molecule fused to peptides, polypeptides or other proteinaceous or non-proteinaceous molecules. In addition, derivatives of apolipoprotein CIII or fragment, derivative, homologue, analogue, chemical equivalent, functional equivalent or mimetic thereof include polymers comprising said apolipoprotein CIII or fragment, derivative, homologue, analogue, chemical equivalent, functional equivalent or mimetic thereof. Preferably, said polymer comprises one or more monomers comprising a polypeptide comprising amino acids 41-79 disclosed in SEQ ID NO: 4. Also preferable are polymers comprising either 2, 3 or 4 monomers comprising a polypeptide comprising amino acids 41-79 disclosed in SEQ ID NO: 4.

Analogues of apolipoprotein CIII contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |

TABLE 2-continued

| Non-conventional amino acid | Code | Non-conventional amino acid | Code |
|---|---|---|---|
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl--aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-α-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |

TABLE 2-continued

| Non-conventional amino acid | Code | Non-conventional amino acid | Code |
| --- | --- | --- | --- |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homobifunctional crosslinkers such as the bifunctional imido esters having $(CH_2)_n$ spacer groups with n=1 to n=6, glutaraldehyde, N-hydroxysuccinimide esters and heterobifunctional reagents which usually contain an amino-reactive moiety such as N-hydroxysuccinimide and another group specific-reactive moiety.

An "effective amount" or an "effective number" means an amount or number necessary to at least partly obtain the desired response, or to delay the onset or inhibit progression of halt altogether, the onset or progression of a particular condition being treated. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "effective amount" is also meant an amount of compound which upon administration is required to prevent, inhibit or reduce blood coagulation or thrombus formation upon administration; or is capable of alleviating or reducing the severity of symptoms associated with the disease or condition mediated by aberrant, unwanted or otherwise inappropriate blood coagulation.

In the method of the invention, apolipoprotein CIII or fragment, derivative, homologue, analogue, chemical equivalent, functional equivalent or mimetic thereof may be administered orally (including buccal, sublingual, inhalation), nasally, rectally, vaginally, intravenously (including intraterially), intradermally, subcutaneously, intramuscularly and topically. Preferably, the apolipoprotein CIII or fragment, derivative, homologue, analogue, chemical equivalent, functional equivalent or mimetic thereof will be formulated into compositions suitable for administration for example with suitable carriers including pharmaceutically acceptable carriers, diluents, thickeners, adjuvants etc. as are routine in the formulation art.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, colouring agents, wetting or emulsifying agents, pH buffering agents, preservatives, and the like. Other suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilised and, if desired, mixed with auxiliary agents, eg. lubricants, preservatives, stabilisers, wetting agents, emulsifiers, salts for influencing osmotic pressure, buffers, colourings, flavourings and/or aromatic substances and the like which do not deleteriously react with substances of the invention. Aqueous suspensions may contain substances which increase the viscosity of the suspension, for example, sodium carboxymethylcellulose, sorbitol and/or dextran. Optionally, the suspension may also contain stabilisers.

Similarly, a "pharmacologically acceptable" salt, ester, amide, pro-drug or derivative of a compound as provided herein is a salt, ester, amide, pro-drug or derivative that this not biologically or otherwise undesirable.

Compositions of the invention which include apolipoprotein CIII or fragment, derivative, homologue, analogue, chemical equivalent, functional equivalent or mimetic thereof may also include additional active ingredients in particular additional anticoagulants (eg. aspirin, warfarin, heparin) and/or thrombolytic agents (eg. streptokinase, tPA, TNKase.™). Dosage forms include solutions, powders, tablets, capsules, gel capsules, suppositories, topical ointments and creams and aerosols for inhalation.

Determining the appropriate route of administration and dosage of the compounds described and used in accordance with the present invention may need to be done on a case-by-case basis by the attending physician or cosmetician. Such determinations are routine to one of ordinary skill in the art (see, for example, Harrison's Principles of Internal Medicine (1998), edited by Anthony Fauci et al., $14^{th}$ edition, published by McGraw Hill).

In general, intravenous doses will be in the range from about 0.1-50 mg/kg of patient body weight per day, preferably 10 mg/kg and 0.3 to 15 mg/kg. Administration may be once or multiple times per day for several days, weeks or years or may be a few times per week for several weeks or years. The amount of compound administered by other routes will be that which provides a similar amount of apolipoprotein CIII or fragment, derivative, homologue, analogue, chemical equivalent, functional equivalent or mimetic thereof in plasma compared to the intravenous amounts described which will take into consideration the plasma bioavailability of the particular apolipoprotein CIII or fragment, derivative, homologue, analogue, chemical equivalent, functional equivalent or mimetic thereof administered.

For oral administration, the apolipoprotein CIII or fragment, derivative, homologue, analogue, chemical equivalent, functional equivalent or mimetic thereof of the present invention can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavouring agents, preservatives, colouring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, International Patent Publication No. WO 96/11698.

For parenteral administration, method of the invention, apolipoprotein CIII or fragment, derivative, homologue, analogue, chemical equivalent, functional equivalent or mimetic thereof may dissolved or suspended in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

Various methods for producing formulations for alimentary delivery are well known in the art. See, generally Remington's Pharmaceutical Sciences, 18$^{th}$ Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 99% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Alternatively, targeting therapies may be used to deliver apolipoprotein CIII or fragment, derivative, homologue, analogue, chemical equivalent, functional equivalent or mimetic thereof more specifically to certain types of cell, by the use of targeting systems such as antibodies or cell specific ligands or specific nucleic genetic material. As used herein the term "genetic material" refers to any single-stranded or double-stranded nucleic acid molecule which at least comprises deoxyribonucleotides and/or ribonucleotides, including DNA (cDNA or genomic DNA), RNA, mRNA, or tRNA, amongst others. The combination of such molecules with non-nucleotide substituents derived from synthetic means or naturally-occurring sources is also contemplated by the present invention. Targeting may be desirable for a variety of reasons, e.g. if apolipoprotein CIII or fragment, derivative, homologue, analogue, chemical equivalent, functional equivalent or mimetic thereof is unacceptably toxic or if it would otherwise require too high a dosage or if it would not otherwise be able to enter the target cells.

Instead of administering the instant apolipoprotein CIII or fragment, derivative, homologue, analogue, chemical equivalent, functional equivalent or mimetic thereof directly, they may be produced in the target cell, e.g. using a viral vector or in a cell based delivery system such as described in U.S. Pat. No. 5,550,050 and International Patent Publication Nos. WO 92/19195, WO 94/25503, WO 95/01203, WO 95/05452, WO 96/02286, WO 96/02646, WO 96/40871, WO 96/40959 and WO 97/12635. The vector could be directed to the target cells. The cell based delivery system is designed to be implanted in a patient's body at the desired target site and contains a coding sequence for apolipoprotein CIII or fragment, derivative, homologue, analogue, chemical equivalent, functional equivalent or mimetic thereof. Alternatively, the apolipoprotein CIII or fragment, derivative, homologue, analogue, chemical equivalent, functional equivalent or mimetic thereof could be administered in a precursor form for conversion to the active form by an activating agent produced in, or targeted to, the cells to be treated. See, for example, European Patent Application No. 0 425 731A and International Patent Publication No. WO 90/07936.

In yet another alternative, stem cells may be isolated, genetically modified to produce, apolipoprotein CIII or fragment, derivative, homologue, analogue, chemical equivalent, functional equivalent or mimetic thereof (constitutively or developmentally) with the cell culture in vivo or ex vivo for regeneration, augmentation or tissue repair therapy.

This method also includes providing a nucleotide sequence encoding apolipoprotein CIII or fragment, derivative, homologue, analogue, chemical equivalent, functional equivalent or mimetic thereof to a cell. This is particularly useful when generating an animal model. Preferably, the nucleotide sequence comprises SEQ ID NO: 1. Also desirable is a nucleotide sequence encoding the lipid binding portion of apolipoprotein CIII and even more preferable is a nucleotide sequence comprising SEQ ID NO: 3. Alternatively, it may be part of a gene therapy approach. A nucleotide sequence encoding apolipoprotein CIII or a part of the gene may be introduced into the cell in a human artificial chromosome (HAC) vector such that the gene remains extrachromosomal. In such a situation, the gene is expressed by the cell from the extrachromosomal location. If a gene portion is introduced and expressed in a cell carrying a mutant target allele, the gene portion should encode a part of the apolipoprotein CIII. Vectors for introduction of genes both for recombination and for extrachromosomal maintenance are known in the art and any suitable vector may be used. Methods for introducing DNA into cells such as electroporation, calcium phosphate co-precipitation and viral transduction are known in the art.

Gene transfer systems known in the art may be useful in the practice of genetic manipulation. These include viral and non-viral transfer methods. A number of viruses have been used as gene transfer vectors or as the basis for preparing gene transfer vectors, including papovaviruses (e.g. SV40, Madzak et al., *J Gen. Virol.* 73: 1533-1536, 1992), adenovirus (Berkner, *Curr. Top. Microbiol. Immunol.* 158: 39-66, 1992; Berkner et al., *BioTechniques* 6; 616-629, 1988; Gorziglia and Kapikian, *J Virol* 66: 4407-4412, 1992; Quantin et al., *Proc. Natl. Acad. Sci. USA* 89: 2581-2584, 1992; Rosenfeld et al, *Cell* 68: 143-155, 1992; Wilkinson et al., *Nucleic Acids Res.* 20: 2233-2239, 1992; Stratford-Perricaudet et al., *Hum. Gene Ther.* 1: 241-256, 1990; Schneider et al., *Nature Genetics* 18: 180-183, 1998), vaccinia virus (Moss, *Curr. Top. Microbiol. Immunol.* 158: 25-38, 1992; Moss, *Proc. Natl. Acad. Sci. USA* 93: 11341-11348, 1996), adeno-associated virus (Muzyczka, *Curr. Top. Microbiol. Immunol.* 158: 97-129, 1992; Ohi et al., *Gene* 89: 279-282, 1990; Russell and Hirata, *Nature Genetics* 18: 323-328, 1998), herpesviruses including HSV and EBV (Margolskee, *Curr. Top., Microbiol. Immunol.* 158: 67-95, 1992; Johnson et al., *J Virol.* 66: 2952-2965, 1992; Fink et al., *Hum. Gene Ther.* 3: 11-19, 1992; Breakefield and Geller, *Mol. Neurobiol.* 1: 339-371, 1987; Freese et al., *Biochem. Pharmacol.* 40: 2189-2199, 1990; Fink et al., *Ann. Rev. Neurosci.* 19: 265-287, 1996), lentiviruses (Naldini et al., *Science* 272: 263-267, 1996), Sindbis and Semliki Forest virus (Berglund et al., *Biotechnology* 11: 916-920, 1993) and retroviruses of avian (Bandyopadhyay and Temin, *Mol. Cell. Biol.* 4: 749-754, 1984; Petropoulos et al., *J Viol.* 66: 3391-3397, 1992), murine (Miller, *Curr. Top. Microbiol. Immunol.* 158: 1-24, 1992; Miller et al., *Mol. Cell. Biol.* 5: 431-437, 1985; Sorge et al, *Mol. Cell. Biol.* 4: 1730-1737, 1984; and Baltimore, *J Virol.* 54: 401-407, 1985; Miller et aL, *J Virol.* 62: 4337-4345, 1988) and human (Shimada et al., *J Clin. Invest.* 88: 1043-1047, 1991; Helseth et al., *J Virol.* 64: 2416-2420, 1990; Page et al., *J Virol.* 64: 5270-5276, 1990; Buchschacher and Panganiban, *J. Virol.* 66: 2731-2739, 1982) origin.

Non-viral gene transfer methods are known in the art such as chemical techniques including calcium phosphate co-precipitation, mechanical techniques, for example, microinjection, membrane fusion-mediated transfer via liposomes and direct DNA uptake and receptor-mediated DNA transfer. Viral-mediated gene transfer can be combined with direct in vivo gene transfer using liposome delivery, allowing one to direct the viral vectors to particular cells. Alternatively, the retroviral vector producer cell line can be injected into particular tissue. Injection of producer cells would then provide a continuous source of vector particles.

In an approach which combines biological and physical gene transfer methods, plasmid DNA of any size is combined with a polylysine-conjugated antibody specific to the adenovirus hexon protein and the resulting complex is bound to an adenovirus vector. The trimolecular complex is then used to infect cells. The adenovirus vector permits efficient binding, internalization and degradation of the endosome before the coupled DNA is damaged. For other techniques for the delivery of adenovirus based vectors, see U.S. Pat. No. 5,691,198.

Liposome/DNA complexes have been shown to be capable of mediating direct in vivo gene transfer. While in standard liposome preparations the gene transfer process is non-specific, localized in vivo uptake and expression may occur, for example, following direct in situ administration.

In another embodiment, a DNA nucleotide sequence encoding apolipoprotein CIII or fragment, derivative, homologue, analogue, chemical equivalent, functional equivalent or mimetic thereof is injected into an animal or human subject. For example, the DNA nucleotide sequence may be that disclosed in SEQ ID NO: 1, variants thereof or fragments thereof. In another embodiment the DNA nucleotide sequence encodes a fragment of apolipoprotein CIII or fragment, derivative, homologue, analogue, chemical equivalent, functional equivalent or mimetic thereof, for example the DNA sequence disclosed in SEQ ID NO: 3.

Injection of the DNA nucleotide sequence may be, for example, to treat a condition characterised by aberrant unwanted or otherwise inappropriate blood coagulation in an animal, for example, a human.

The DNA sequence encoding an apolipoprotein CIII or fragment, derivative, homologue, analogue, chemical equivalent, functional equivalent or mimetic thereof may be injected alone, or in combination with other drugs and/or agents. The DNA sequence may be prepared as a pharmaceutical composition. The composition may contain one or more added materials such as carriers and/or excipients described herein.

Although a naked DNA nucleotide sequence may be injected in accordance with this invention, it is preferable that the injected DNA be accompanied by a carrier, for example, Felgner et al., U.S. Pat. No. 5,459,127, the disclosure of which is incorporated in its entirety herein by reference.

The apolipoprotein CIII or fragments, derivatives, homologue, analogue, chemical equivalent or mimetic thereof of the invention may also be used as an additive to blood samples or reserves in order to inhibit or prevent coagulation. Accordingly, there is provided a method for producing an anticoagulation effect in a sample of blood, said method comprising introducing to said sample of blood, an effective amount of apolipoprotein CIII or fragment, derivative, homologue, analogue, chemical equivalent, functional equivalent or mimetic thereof.

The present invention is further described in the following non-limiting examples.

EXAMPLE 1

Materials and Methods

Preparation of Human Plasma Fraction

Human plasma was used to prepare fractions that were largely devoid of abundant, high molecular weight proteins. Frozen plasma was rapidly thawed in a 37° C. water bath and 1 volume of acetonitrile was added. Following a 10 minute incubation at room temperature, precipitated high molecular weight proteins were removed by centrifugation at 3000×g and the supernatant transferred to a fresh tube. In some preparations, urea was added to plasma to a final concentration of 2M prior to acetonitrile precipitation. MALDI-MS analysis of these plasma fractions demonstrated that the majority of proteins recovered were <40 kD. Serum was substituted for plasma on occasion to prepare a similar fraction from serum.

Bioassay of Anti-Coagulation Activities Contained in Human Plasma Libraries

The two major arms of the blood coagulation cascade, the intrinsic and extrinsic pathways, ultimately converge to mediate the cleavage of fibrinogen to fibrin and initiate clot formation. The Activated Partial Thromboplastin Time (APTT) test and the Prothrombin Time (PT) test are routinely used in the clinic to assess the functionality of the intrinsic and extrinsic pathways respectively. Described here is the development of APTT and PT tests that have been adapted for 96 well microplates in a rapid and fully automated format that suits the large scale screening of large numbers of compounds suitable for drug discovery applications.

The coagulation assays rely on the collection of human blood using 0.32% tri-sodium citrate as anticoagulant. Platelet poor plasma (PPP) is collected following centrifugation of citrated blood by routine procedures.

Both PT and APTT assays were assembled automatically using robotic liquid handling instrumentation such as the Multiprobe II EX Robotic Liquid Handling System (Perkin Elmer Life Sciences). Fresh or rapidly thawed human PPP (50 µl) is added to the wells of a clear bottom black 96 well plate followed by transfer of test compounds (1-10 µl) from 96 well library plates. Appropriate vehicle controls are added in place of library compounds in some wells. The test plate is transferred to a plate shaker and the compounds are pre-incubated with PPP for a defined period (5-20 minutes) at 20-37° C. with orbital shaking. For the PT assay, the microplate is then transferred to a laser-based microplate nephelometer (NEPHELOstar Galaxy, BMG Labtechnologies) and pre-equilibrated to 37° C. All wells of the assay plate are then automatically injected with a commercially available PT reagent via the NEPHELOstar Galaxy to initiate coagulation. A range of commercially available reagents have been successfully tested and include, but are not limited to PT-Fibrinogen Recombinant (Instrumentation Laboratory).

For the APTT assay, all wells of the assay plate receive an equivalent volume of commercially available APTT reagent via the robotic liquid handling instrument after pre-incubation with library compounds. A range of commercially available reagents have been successfully tested and include, but are not limited to PTT-A reagent (Diagnostica Stago). The microplate is then loaded into a laser-based microplate nephelometer (NEPHELOstar Galaxy, BMG Labtechnologies Germany), equilibrated to 37° C. and the coagulation assay is initiated via automated injection of 25 mM $CaCl_2$ (volume equivalent to original PPP volume). Automated plate shaking is then performed using optimal conditions in either orbital or linear mode at a width of between 1-7 mm for a defined period prior to the first measurement interval. To generate precise kinetic curves, the measurement windows can be set to read as frequently as 0.2 seconds, but are routinely set at 2-3 seconds for the PT and APTT assays respectively. Automated laser-based nephelometry of each well sensitively detects time-dependent induction of coagulation as an increase in relative light scatter and gives coagulation times with both tests that are comparable to other methods used clinically.

MALDI-TOF MS Identification of Active Components

All active fractions were mass analysed using a Bruker Autoflex matrix assisted laser desorption/ionization (MALDI) mass spectrometer run in linear as well as reflector positive ion mode. An aliquot of 0.5 µl of sample was mixed with 0.5 µl of 2.5 dihydroxybenzoic acid matrix directly on the sample target and left to dry prior to insertion into the instrument.

The mass of the intact apolipoprotein $CIII_{2-1-0}$ were measured to 9712 Da, 9421 Da and 8765 Da, respectively.

Following the initial mass measurement, the protein in highest abundance ($CIII_1$) was fragmented by changing the laser settings. A 'post source decay'(MALDI-PSD-MS) spectrum was obtained and the presence and size of carbohydrate moiety was determined to be a sialic acid residue, an N-acetylhexose and a hexose. This result is confirmed in the literature. Then an 'in source decay'(MALDI-ISD-MS) spectrum was recorded (FIG. 5) and peaks corresponding to 63 of the amino acid residues of the primary sequence was obtained. The spectrum was annotated using the XMASS program, transferred to BioTools—an investigative program. By comparing the mass information to the SwissProt protein database an unambiguous identification of the protein as Apolipoprotein CIII was obtained.

Isolation and Characterisation of a Prothrombin Time Inhibitor

Figure 1:
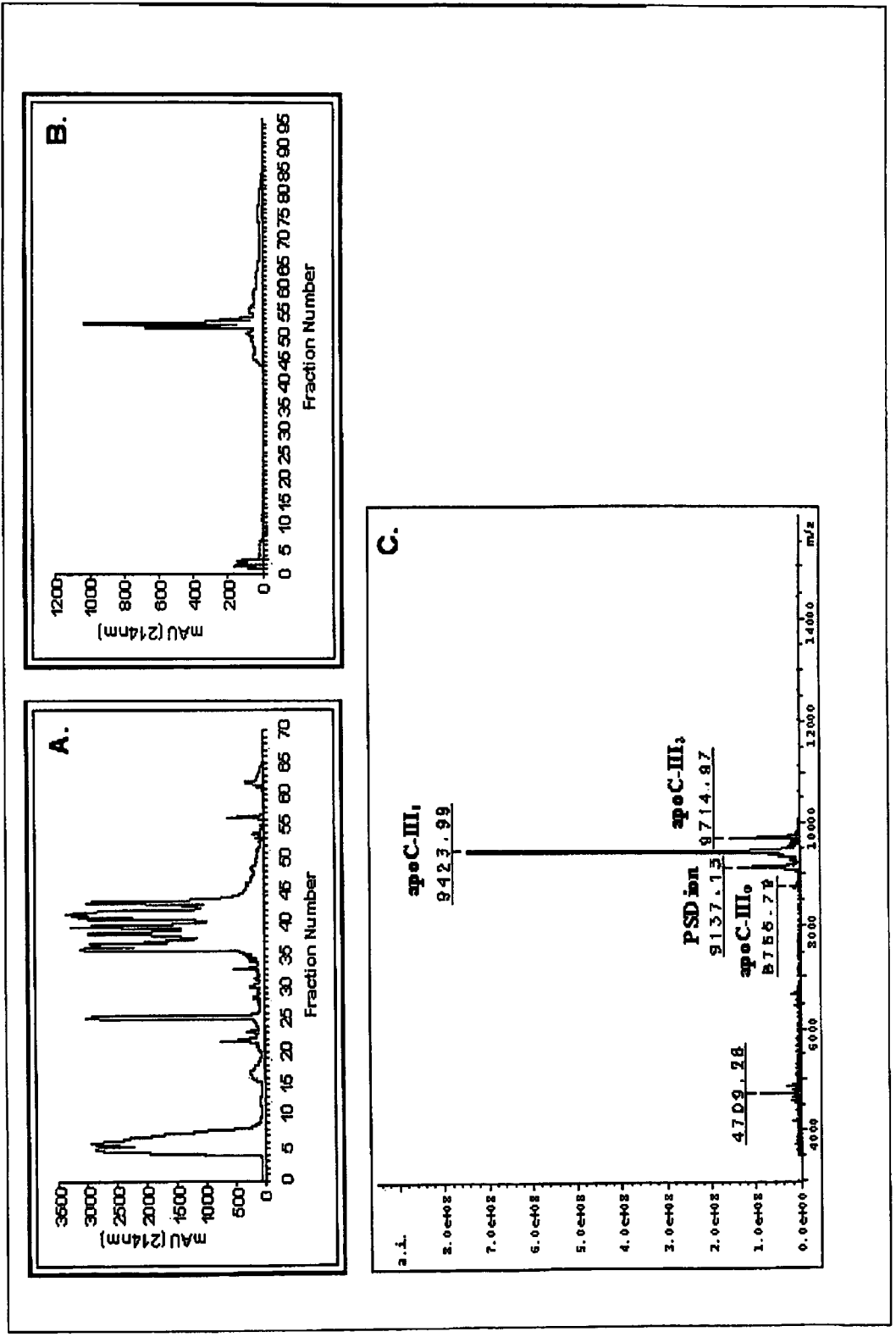
FIG. 1. Chromatographic separation and identification of apolipoprotein CIII

Initial libraries were established using 5 mg of soluble protein isolated from human plasma following precipitation with 1 volume of acetonitrile. Separation of this material was achieved by reversed phase chromatography on a Zorbax 300SB-C18 column (4.6×250 mm) using a linear gradient of 0-70% solvent B over 30 minutes at a flow rate of 1 ml/min. Solvent A consisted of 0.1% trifluoroacetic acid (TFA) in Milli-Q $H_2O$ and solvent B consisted of 0.08% TFA in acetonitrile. The chromatographic separation was monitored at 214 nm (FIG. 1A). Fractions were collected at 1 min intervals directly into 96 well polypropylene library plates, lyophilized and library fractions were then reconstituted in 50-100 µl 25 mM $NH_4HCO_3$ for bioassay. An automated liquid handling robot was used to dispense 5 µl aliquots of library fractions into individual wells of 96 well assay plates containing 50 µl of human platelet poor plasma (PPP) for determination of Prothrombin Time as described above. The prothrombin time indicates the time at which coagulation is initiated and is detected by an increase in light scatter by the nephelometric method employed. PPP pre-incubated with vehicle only returned a PT of 16 seconds (FIG. 2). Two individual fractions from this library (fractions 40 and 41) consistently delayed the induction of the coagulation response as measured by PT (FIG. 1). In the presence of fraction 40, PT was increased to 18 seconds (+12.5%) while fraction 41 increased PT to 24 seconds (+50%). Similar inhibitory responses were detected when identical libraries were prepared from plasma derived from multiple different donors or from human serum. The same fractions (40, 41) had no measurable effect on the intrinsic arm of the coagulation patwhway as measured by Activated Partial Thromboplastin Time (APTT).

The major inhibitory fraction (#41) from the initial separation was subjected to a second chromatographic separation to isolate the active components. In this case, separation was achieved by reversed phase chromatography on a Zorbax 300SB-C18 column (2.1×150 mm) using a linear gradient of 0-100% solvent B over 91 minutes at a flow rate of 0.5 ml/min (FIG. 1B). Solvent A consisted of 10 mM $NH_4HCO_3$ in Milli-Q $H_2O$, pH 8 and solvent B consisted of 10 mM $NH_4HCO_3$ in 70% acetonitrile, pH 8. The chromatographic separation was monitored at 214, 254 and 280 nm and fractions were collected at 1 minute intervals directly into 96 well polypropylene library plates prior to lyophilization and reconstitution in 50 µl 25 mM $NH_4HCO_3$ for bioassay. Following bioassay of the second dimension library in a PT assay, three fractions (#53-55) were detected that inhibited PT to varying degrees (FIG. 3). The control PT of 16 seconds was prolonged to 18 seconds (+12.5%) by fraction 53, to 20 seconds (+25%) by fraction 54 and to 17 seconds (+6.25%) by fraction 55.

Analysis of these active fractions by MALDI-mass spectrometry revealed the presence of various isoforms of apolipoprotein CIII that differed with respect to the extent of glycosylation. Human apolipoprotein CIII exists in three forms depending upon the level of sialylation: $C-III_0$, $C-III_1$, and $C-III_2$. The subscript indicates the number of sialic acid residues. Fractions 54 and 55 were shown to contain predominantly apolipoprotein $C-III_1$, (average mass of 9421) and fraction 53 contained relatively lower amounts of apolipoprotein $C-III_2$ (average mass of 9712 consistent with previous reports showing that Apolipoprotein $CIII_1$, is by far the most abundant form present in human plasma. This compound has been referred to in-house as ART1.

Tryptic Peptides of Apolipoprotein CIII Inhibit Prothrombin Time

To determine whether smaller peptides derived from apolipoprotein CIII could similarly act as PT coagulation inhibitors, limited tryptic digestion was performed on apolipoprotein CIII. As starting material, fractions 40/41 (confirmed as active by bioassay) from an initial low pH C18 separation was pooled and digested with trypsin. The tryptic digest was carried out in 25 mM $NH_4HCO_3$, 10% acetonitrile, pH 8 at 37° C. for 2 hours and was monitored by MALDI- MS. The tryptic digest was then separated by reversed phase chromatography on a Zorbax 300SB-C18 column (2.1×150 mm) using a linear gradient of 0-100% solvent B over 91 minutes at a flow rate of 0.5 ml/min. Solvent A consisted of 10 mM $NH_4HCO_3$ in Milli-Q $H_2O$, pH 8 and solvent B consisted of 10 mM $NH_4HCO_3$ in 70% acetonitrile, pH 8. The chromatographic separation was monitored at 214, 254 and 280 nm. Fractions were collected at 1 minute intervals into 96 well polypropylene library plates prior to lyophilization and reconstitution in 30-50 µl 25 mM NH₄HCO₃ for bioassay. Four fractions (#42-45) were found to contain peptides that delayed the PT response by as much as 87% (FIG. 4). All of these fractions contained predominantly peptide 41-79 of apolipoprotein CIII and were shown by MALDI-mass spectrometry to vary only with respect to the degree of glycosylation as outlined in Table 3.

TABLE 3

MALDI-MS determination of tryptic apolipoprotein peptides present in PT inhibitory fractions.

| Fr. No. | amino acids (from-to) | Mass | Carbohydrate |
|---|---|---|---|
| 42 | 41-79 | 5383.6 | N-acetylgalactosamine-galactose + 2 sialic acid |
| 43 | 41-79 | 5092.3:5383.6 | N-acetylgalactosamine-galactose + 1 sialic acid:2 sialic acid |
| 44 | 41-79 | 5092.3:4801.1 | N-acetylgalactosamine-galactose + 0 sialic acid:1 sialic acid |
| 45 | 41-79 | 4447.1 | no carbohydrate |

EXAMPLE 2

A fragment of apolipoprotein CIII corresponding to amino acids 41-79 (SEQ ID NO:4), designated CR001 (hereinafter in Examples 2-6 referred to as "the apolipoprotein CIII fragment") was synthesized for further testing of its inhibitory effect in ex vivo PT assays. Various concentrations of the apolipoprotein CIII fragment were pre-incubated with the commercially available thromboplastin reagent PT-Fibrinogen recombinant (Instrumentation Laboratories) and this mixture was used to initiate coagulation of citrated human plasma. Laser-based microplate nephelometric assays were used to determine PT as described earlier. Concentrations of the apolipoprotein CIII fragment shown in FIG. 6 relate to final assay concentrations of peptide. FIG. 6 demonstrates that the apolipoprotein CIII fragment causes a dose-dependent delay in PT, with an approximate doubling of PT achieved with 28 µM of the apolipoprotein CIII fragment. A single concentration of full-length Apo CIII purified from human plasma is shown for comparison. The inhibitory responses on ex vivo PT coagulation mediated by the apolipoprotein CIII fragment indicate that the amino acids corresponding to SEQ ID NO:4 may encompass the majority of sequence required to produce this anticoagulant effect. In addition, studies with the apolipoprotein CIII fragment suggest that the differential glycosylation of natural Apolipoprotein CIII is not strictly required for mediating this anticoagulant action.

EXAMPLE 3

The apolipoprotein CIII fragment was also tested for its ability to inhibit tissue factor-mediated coagulation in whole human blood. Freshly obtained citrated whole human blood was reacted with various concentrations of the synthetic and commercial thromboplastin reagent as described for FIG. 6 and the subsequent coagulation response was determined by nephelometric measurement. As for citrated human plasma, increasing concentrations of peptide caused a progressive inhibition of tissue factor mediated coagulation of whole human blood, with a similar does-response to that demonstrated in plasma.

The data presented in FIGS. 6 and 7 demonstrate a distinct anticoagulant effect of the apolipoprotein CIII fragment in ex vivo PT assays using either human plasma or whole blood. The apolipoprotein CIII fragment (0.85-42 µM) had no effect on APTT coagulation in human citrated plasma, indicating that the effects of the apolipoprotein CIII fragment are limited to the extrinsic arm of the coagulation pathway. Taken together, these data support the claims of the invention that Apolipoprotein CIII (and/or fragments thereof) are capable of producing an anticoagulant effect by targeting components of the TF:VIIa complex.

EXAMPLE 4

To further delineate the level at which Apolipoprotein CIII and the apolipoprotein CIII fragment were acting to inhibit TF-mediated coagulation, their effects were tested in a two stage chromogenic substrate assay that relies on the TF:VIIIa mediated conversion of Factor X to Factor Xa; activity of Factor Xa is then determined using the chromogenic substrate S-2765. Reactions were established in microplate by incubating various concentrations of Apolipoprotein CIII or apolipoprotein CIII fragment with TF (1:200 dilution of PT-Fibrinogen recombinant), human Factor VIIIa (133 pM) and bovine Factor X (0.25 U/ml) in a 60 µl reaction containing 50 mM Tris (pH 7.4), 100 mM NaCl, 4 mM CaCl₂ and 0.1% BSA for 10 minutes at 37° C. The microplate was rapidly transferred to a plate reader, and 50 µl of the chromogenic substrate S-2765 was added to a final concentration o 0.9 mM. Timed absorbance readings ($A_{405}$ nm) were immediately commenced at 30 second intervals for 7 minutes to determine Factor Xa activity.

As shown in FIG. 8A, a preparation of Apolipoprotein CIII purified from plasma derived from multiple human donors led to a dose-dependent inhibition of Factor Xa activity. The calculated $IC_{50}$ for apolipoprotein CIII was 7.2 µM. The apolipoprotein CIII fragment (FIG. 8B) was also shown to cause dose-dependent inhibition of Factor Xa activity in this 2-stage chromogenic substrate assay. The calculated $IC_{50}$ for synthetic peptide the apolipoprotein CIII fragment was 6.1 µM and greater than 90% inhibition was achieved with an apolipoprotein CIII fragment concentration of around 100 µM.

These data demonstrate that apoliproprotein CIII and the apolipoprotein CIII fragment, have indistinguishable inhibitory actions at the level of the TF:VIIa:X/Xa complex. Since neither apolipoprotein CIII nor the apolipoprotein CIII fragment have any demonstrable action on the APTT coagulation pathway, it is unlikely that these peptides interfere with factor X or Xa activity directly. To further support this notion, it was shown that neither apoliproprotein CIII nor the apolipoprotein CIII fragment have any direct inhibitory effect on factor Xa activity when tested alone on the chromogenic substrate S-2765. In the absence of any demonstrable direct effect on factor Xa activity, it is proposed that the TF:VIIa complex is the most likely target of apoliprotein CIII and its derivative apolipoprotein CIII fragment.

EXAMPLE 5

The inhibitory effects of the apolipoprotein CIII fragment on PT coagulation responses were tested in plasma derived from a variety of species in nephelometric based assays as previously described. Shown in FIG. 9 is the response to a single concentration of the apolipoprotein CIII fragment (22 µM) in various plasmas all initiated with the same TF preparation (PT-Fibrinogen Recombinant, Instrumentation Laboratories). The data demonstrate an obvious differential response, with the apolipoprotein CIII fragment having substantial inhibitory effects in human and porcine plasma, lesser effects in rabbit and mouse plasma and no discernible effect at this concentration in canine and rat plasma. Since the TF preparation used to initiate coagulation in all species is identical, these data suggest that the apolipoprotein CIII fragment interacts with a plasma factor in addition to TF, or alternatively a factor other than TF.

Collectively, the data presented in FIGS. 6-9 suggest that factor VIIa represents the most likely target for interaction with apolipoprotein CIII and apolipoprotein CIII fragment, either alone or in complex with TF.

EXAMPLE 6

Preliminary studies with a range of apolipoprotein CIII fragment derived peptides indicate that the major anticoagulant activity is derived from the N-terminal portion of the apolipoprotein CIII fragment. Several apolipoprotein CIII fragment-derived peptides depicted in FIG. 10 were tested for relative inhibitory activity in a 2-stage chromogenic substrate assay that determines TF:VIIa-mediated activation of factor X. Peptides designated CR003, CR004 and CR005 that correspond to various C-terminal fragments of the apolipoprotein CIII fragment encompassing amino acids 59-79, showed no inhibitory activity in the chromogenic substrate assay. In contrast, peptide CR002 (amino acids 41-60) retained the ability to inhibit TF:VIIa mediated activation of factor X, but at much lower potency than the apolipoprotein CIII fragment. Progressive loss of potency was shown as additional N-terminal residues were removed (CR006; amino acids 49-62).

The invention claimed is:

1. A method for the prophylactic and/or therapeutic treatment of a condition characterised by the aberrant, unwanted or otherwise inappropriate blood coagulation in a subject, said method comprising administering to said subject, an effective amount of a composition comprising apolipoprotein CIII or a lipid binding fragment of apolipoprotein CIII, wherein said lipid binding fragment of apolipoprotein CIII comprises amino acids 41-79 of apolipoprotein CIII.

2. The method according to claim 1 wherein said condition is selected from the group consisting of deep vein thrombosis, pulmonary embolism, thromboembolic complications associated with atrial fibrillation, cardiac valve replacement, percutaneous transluminal angioplasty, ischemia-reperfusion injury and post-operative thromboembolism.

3. The method according to claim 1 where said subject is a mammal.

4. The method according to claim 3 wherein said mammal is a human.

5. The method according to claim 1 wherein said composition comprises additional active ingredients, wherein said additional active ingredients are an additional anticoagulant and/or a thrombolytic agent.

* * * * *